United States Patent
Harris, Jr.

(10) Patent No.: US 6,743,756 B2
(45) Date of Patent: *Jun. 1, 2004

(54) SUSPENSIONS OF PARTICLES IN NON-AQUEOUS SOLVENTS

(75) Inventor: William Franklin Harris, Jr., Friendswood, TX (US)

(73) Assignee: Benchmark Research and Technology, Inc., Midland, TX (US)

( * ) Notice: Subject to any disclaimer, the term of this patent is extended or adjusted under 35 U.S.C. 154(b) by 111 days.

This patent is subject to a terminal disclaimer.

(21) Appl. No.: 09/905,358

(22) Filed: Jul. 13, 2001

(65) Prior Publication Data

US 2002/0193256 A1 Dec. 19, 2002

Related U.S. Application Data

(63) Continuation-in-part of application No. 09/771,226, filed on Jan. 26, 2001.

(51) Int. Cl.⁷ ................................................. C09K 3/00
(52) U.S. Cl. ................. 507/261; 507/265; 507/273; 507/209; 507/211; 507/207; 507/216; 507/224; 507/939; 524/275; 524/72; 525/403; 525/409; 516/104; 516/109; 516/108; 106/17; 106/18; 106/18.29; 424/401; 424/70.22; 424/405
(58) Field of Search ................................ 507/261, 265, 507/273, 209, 211, 269, 207, 216, 224, 939; 524/275, 72; 525/403, 409; 516/104, 109, 108; 106/17, 18, 18.29

(56) References Cited

U.S. PATENT DOCUMENTS

| | | | | |
|---|---|---|---|---|
| 3,629,398 A | * | 12/1971 | Schmitt | 516/104 |
| 3,670,065 A | * | 6/1972 | Eriksson | 524/275 |
| 3,780,170 A | * | 12/1973 | Goodhart | 524/275 |
| 4,620,596 A | | 11/1986 | Mondshine | 166/292 |
| 4,673,526 A | | 6/1987 | Zabotto et al. | 252/174.16 |
| 5,091,448 A | | 2/1992 | Hostettler et al. | 524/45 |
| 5,169,552 A | | 12/1992 | Wise | 252/95 |
| 5,205,953 A | | 4/1993 | Dixit | 252/94 |
| 5,279,755 A | | 1/1994 | Choy et al. | 252/76 |
| 5,304,376 A | | 4/1994 | Friedrichs et al. | 424/409 |
| 5,468,418 A | | 11/1995 | Rabone | 252/174.25 |
| 5,565,513 A | | 10/1996 | Kinsey, III et al. | 524/405 |
| 5,631,313 A | | 5/1997 | Bishop et al. | 524/45 |
| 5,648,421 A | * | 7/1997 | Thiele | 524/275 |
| 5,707,551 A | | 1/1998 | Pallas et al. | 252/308 |
| 5,834,533 A | | 11/1998 | Patel et al. | 523/130 |
| 5,863,647 A | | 1/1999 | Yoneda et al. | 428/331 |
| 5,879,705 A | * | 3/1999 | Heafield | 424/464 |
| 5,906,962 A | | 5/1999 | Pallas et al. | 504/116 |
| 5,925,182 A | | 7/1999 | Patel et al. | 106/266 |
| 5,969,012 A | | 10/1999 | Harris, Jr. | 524/55 |
| 5,985,252 A | | 11/1999 | Hall et al. | 424/65 |
| 5,985,801 A | | 11/1999 | Hoff | 507/216 |

* cited by examiner

Primary Examiner—Philip C. Tucker
(74) Attorney, Agent, or Firm—Christopher L. Makay

(57) ABSTRACT

Liquid suspensions of particles in non-aqueous solvents are extremely stable over long periods of time with minimum separation of the solvent and no hard packing of the dispersed particles. The suspensions enable a user to rapidly add the suspension to water and to mix at low speeds without generating fugitive dust in the process. In addition, a liquid dispersion can provide an easy to use liquid containing higher concentrations of the active dispersed phase than can be accomplished by simply preparing an aqueous solution of the dispersed phase. Alternatively, highly water-soluble particles may also be suspended which have poor storage, freeze/thaw, or heat/cool stability. In some cases, liquid dispersions can yield controlled release of the dispersed phase because the dispersed phase is not in aqueous solution. The suspensions are environmentally safe and biodegradable and may be used in environmentally sensitive applications, such as for oil well treating fluids for offshore areas. The suspensions exhibit minimal oil or grease upon dilution and contain no surfactants that which can sometimes add to the oil and grease determination. The suspensions and the fluids produced by diluting the fluids to a working concentration of dispersed phase exhibit low toxicity to marine organisms and to humans. The suspension can be manufactured from ingredients suitable for use in personal care applications, such as cosmetics, shampoos and the like; from ingredients suitable for use in indirect contact with food; and from ingredients that are exempt from regulations as adjuvants for agricultural pesticides.

81 Claims, No Drawings

SUSPENSIONS OF PARTICLES IN NON-AQUEOUS SOLVENTS

CROSS-REFERENCE TO RELATED APPLICATIONS

This application is a continuation-in-part of application Ser. No. 09/771,226, which was filed Jan. 26, 2001.

BACKGROUND OF THE INVENTION

1. Field of the Invention

The present invention relates to stable concentrated non-aqueous suspensions of particles with excellent storage stability. More specifically, the particle suspensions are characterized by having a medium of low molecular weight polyalkylene glycol and a stabilizer of a hydrogenated castor wax.

2. Description of the Related Art

Heretofore, in preparing aqueous dilutions of particles, it has been necessary to utilize solid ingredients that are mixed with water or other aqueous fluid at the job site. A number of disadvantages are inherent in such mixing procedures, particularly when large volumes of solutions are prepared. For example, special mixing equipment for mixing the dry additives with water is required and problems such as chemical dusting, uneven mixing, and extended preparation and mixing time are involved. In addition, the mixing and physical handling of large quantities of dry chemicals require a great deal of manpower, and, where continuous mixing is required, the accurate and efficient handling of chemicals is extremely difficult.

In addition, when particles are used, they are typically added to water to make a dilute solution, resulting in the generation of fugitive dust. This dust has a number of potential detrimental effects. Workers preparing the solution can inhale the dust, and some of the particles that can be suspended in a non-toxic solvent produce dust when handled in a powdered form. This may produce a respiratory allergenic response, irritation, or other toxic effect when inhaled. Dust can also drift to areas where it is not intended.

In the agricultural industry, many handling problems may arise when one is forced to prepare aqueous end-use formulations and/or slurries from solids, especially active solids, e.g. wettable bioactive powders. Farmers preparing tank mixes of herbicides, insecticides and/or other bioactives from solids for applications to crops and soil are exposed to certain safety hazards and inconveniences due to the generation of noxious dusts which may be irritable to the skin and hazardous to breathe.

Additionally, finely ground powders, even so-called powders, of many water-soluble bioactives do not disperse well when prepared as tank mixes. They have poor spontaneity or "bloom" and have low suspendability. They have poor re-dispersibility and are incompatible with other bio-actives as compared to liquid bioactive concentrates. Thus, final formulators, such as farmers, when preparing diluted aqueous active compositions find that the handling and application of solids materials, such as fertilizers, are much easier if the material can be supplied in a fluid rather than solid form. Economics then dictate that the active material be supplied in a highly concentrated fluid to the final formulator.

Saturation solubility in water of many water-soluble active constituents, such as potassium chloride, is too low to make it economical for supply to the end-user simply in the form of a solution. Alternatively, highly concentrated suspensions of water-soluble compounds, both in water and in organic liquids, have very poor storage, freeze/thaw, and heat/cool stability. As a result of the spontaneous crystal dissolution-recrystallization process, there occurs a progressive increase in the size of the particulate active material. This increase in particle size results in settling, bleed and changes in visco-elastic properties and thus severely limits concentrate loading levels.

To avoid lump or dust formation and its associated problems, the particles can be added to the aqueous systems as liquid slurries or suspensions. There currently exists a number of methods for accomplishing this, and the compositions prepared thereby. These methods often employ use oil carriers (e.g., mineral, isoparaffin or diesel) to suspend and deliver the particles to the aqueous systems. In applications where the materials may be used in off-shore oil well treatment fluids which may be eventually discharged into the environment, recent regulations by the Environmental Protection Agency limit the amount of oil or grease that can be used in offshore oilfield applications for well treatment fluids. The National Pollutant Discharge Elimination System (NPDES) General Permit issued on Apr. 19, 1999 (Federal Register Vol. 64 No. 74) limits the oil and grease to a daily maximum concentration of 42 mg/l and a monthly average of 29 mg/l when the suspension is diluted to the intended use level with fresh or salt water. Unlike the liquid suspensions that contain diesel fuel or other hydrocarbon solvents the suspensions of the present invention contain minimal detectable oil or grease when diluted to the concentration appropriate for well treatment.

U.S. Pat. No. 5,091,448 discloses a suspending medium for a water-soluble polymer, while U.S. Pat. No. 5,631,313 discloses a suspending medium for particles. These two patents utilize isoparaffin oils as the solvent for the suspensions where a styrene/isoprene copolymer is used as the suspension agent. Upon dilution to the intended use concentration in fresh or salt water for a well treatment fluid, the dilution contains a much higher concentration of oil and grease than is permitted by the above regulations. Furthermore the styrene/isoprene copolymer that is used to stabilize the suspension is insoluble in water miscible solvents such as the polyalkylene glycols of the present invention.

U.S. Pat. No. 5,925,182 discloses a stable liquid suspension composition including a liquid carrier, a solid fatty acid or a salt thereof, and a solid particulate wherein the liquid carrier is selected from the group consisting of oils, olefins, terpenes, glycols, esters, ethers, alcohols, and combinations of any two or more thereof and the liquid carrier, solid fatty acid or salt thereof, and solid particulate are each present in the composition in a stabilizing amount sufficient to produce a stable liquid suspension. Also disclosed is a stable liquid composition including a liquid carrier, an oil soluble polymer, and a solid particulate wherein the liquid carrier is selected from the group consisting of olefins, terpenes, esters, and combinations of any two or more thereof and the liquid carrier, oil-soluble polymer, and solid particulate are each present in the composition in a stabilizing amount sufficient to effect the formation of a stable liquid suspension. Although this patent includes some solvents that may be environmentally friendly and some that contribute to oil and grease as measured by the EPA method, the suspension agent is based on a fatty acid or salt thereof, or an oil soluble polymer, either of which will be measured as oil and grease.

In addition to the oil carrier fluid, many hydrocarbon solvent based slurries usually contain clay or clay like particulates that act to viscosity and stabilize the non-aqueous suspension. The clay component itself is also often times an undesirable component. This is particularly true in oil and gas field applications where incorporation of the clay into the slurries, which is necessary to keep the particles in suspension, impairs the permeability of the oil or gas bearing strata. This is the very same problem caused by the formation of lumps that the oil suspension or slurry is supposed to eliminate.

Many aqueous suspensions include a variety of inorganic and organic particles that use water as the continuous phase for preparing the liquid solution or suspension. While the use of water is certainly environmentally acceptable and reduces the dusting properties of many solid particles, its use is counterproductive with many solids. Among these are solids that may be reactive with water. Also, particles may be wholly or partially soluble in water and this solubility may limit the maximum concentration of the dispersed phase that can be incorporated into an aqueous suspension. The use of a non-solvent for suspending certain solids results in a controlled release of the solids because the particles must first dissolve into water before they become functional.

U.S. Pat. No. 4,673,526 discloses an anhydrous skin cleansing composition containing an oil phase, an emulsifying agent, and particulate water soluble polymeric abrasive particles. This compound contains an oily phase, at least one emulsifying agent, and at least one abrasive substance. The compound is presented in anhydrous form and the abrasive substance in suspension in the oily phase is highly hydrosoluble with an average particle size between 50 and 1000 microns. This compound allows the deep cleansing of the skin through exfoliant action.

U.S. Pat. No. 5,985,252 discloses a suspension antiperspirant composition for topical application to the human skin including from 10 to 26% by weight of the composition of a solid particulate antiperspirant active suspended in a cosmetic base. The antiperspirant active includes a blend of an antiperspirant active with relatively small particles with a volume average particle size in the range of from 0.5 to 8 micrometers and an antiperspirant active with relatively large particles having a volume average particle size in the range of larger than 12 to smaller than 50 micrometers with the weight ratio of the antiperspirant active having smaller particles to the antiperspirant active having larger particles in the composition is in the region of 5:1 to 1:5 by weight.

U.S. Pat. No. 5,863,647 discloses a monodisperse glycol suspension having excellent dispersion stability at a pH within a wide range. The suspension includes a monodisperse suspension in a glycol of spherical fine particles of an amorphous inorganic oxide having an average particle diameter of 0.15 to 5 micrometers and a relative particle size standard deviation of 1.0 to 1.5 and containing glycol bonded to its surface in amounts of 0.003 to 5 millimoles glycol, per gram of fine particles. This monodisperse suspension is useful as a raw material for the production of a polyester film having improved slipperiness.

Despite the above teachings, there still exists a need for liquid suspensions for water-soluble polymers that are environmentally friendly; suitable for use in personal care products, such as cosmetics and shampoos and the like; can be manufactured using ingredients suitable for use in indirect contact with food or as a pesticide adjuvant; are extremely stable over long periods of time and are operative over a wide temperature range; and are comprised of materials that are commercially available or easy to manufacture.

SUMMARY OF THE INVENTION

In accordance with the present invention, a non-aqueous suspension includes solid particles, liquid polyalkylene glycol, and a suspension stabilizer of a hydrogenated castor oil or wax. The non-aqueous suspension includes the solid particles in an amount between about 0.1 and about 75 percent by weight of the suspension, the liquid polyalkylene glycol in an amount between about 24 and about 99.8 percent by weight of the suspension, and the suspension stabilizer in an amount between about 0.1 and about 5.0 percent by weight of the suspension. The non-aqueous suspension may further include one or more of the following additive materials: proppants, antifoaming agents, surfactants, corrosion inhibitors, pH buffers, and preservatives.

The liquid polyalkylene glycol includes polyethylene glycol, polypropylene glycol, ethylene oxide propylene oxide block copolymers, and mixtures thereof. The liquid polyalkylene glycol may include between about 0.1 and 4% by weight of the polyalkylene glycol of a thickener including partially neutralized polyacrylic acid, hydroxypropyl cellulose, hydroxypropyl guar, fumed silica, hydrophobic silica, and mixtures thereof.

The solid particles include non-polymeric particles that are either inorganic particles or organic particles. The inorganic particles include boron compounds; alkaline earth peroxides; magnesium peroxide or calcium peroxide; iron oxide; calcium aluminate, calcium carbonate, magnesium carbonate, calcium oxide, magnesium oxide, calcium hydroxide and magnesium hydroxide and mixtures thereof; and siliceous or ceramic particles. The organic particles include gilsonite; lignosulfonates and the sodium, potassium, ammonium, calcium and magnesium salts thereof; and ethylenediaminetetraacetic acid and the salts thereof. The particles further include fertilizers selected from the group consisting of potassium nitrate, ammonium dihydrogenphosphate, ammonium nitrate, sodium nitrate ammonium phosphate, ammonium polyphosphate, potassium hydrogen phosphate, disodium hydrogen phosphate, urea, and mixtures thereof. The particles still further include pesticides selected from the group consisting of boric acid, butocarboxime, acephate (O,S,-dimethyl acetylphosphoramidothioate), dimethoate, dimehypo (disodium salt of dihydrogen S,S'-(2-dimethylaminotrimethylene)di(thiosulfate)) vamidothion (O,O-dimethyl S-2-(1-methylcarbamoylethylthio)ethyl phosphorothioate), methoxyl (S-methyl (EZ)-N-(methylcarbamoyloxy)thioacetamide) and mixtures thereof. The particles even further include herbicides selected from the group consisting of dalapon (2,2 dichloropropirionic acid, sodium salt) ammonium sulfamate (2,2-dichloropropionic acid (2,2 dichloropropirionic acid, sodium salt) ammonium sulfamate), dicamba (3,6-dicloro-o-anisic acid), cacodylic acid, fomesafen (5-(2-chloro-α,α, α-trifluoro-p-tolyloxy)-N-methylsulfonyl-2-nitrobenzamide); glyphosate (N-(phosphonomethyl) glycine) and mixtures thereof. The particles yet further include fungicides selected from the group consisting of copper sulfate, fosetyl-Al aluminum tris (O-ethyl phosphonate) (ethyl hydrogen phosphonate aluminum tris (O-ethyl phosphonate)), benalaxyl (methyl N-phenylacetyl-N-2,6-xylyl-DL-alaninate), guazatine (iminoctadine ($C_{18}H_{41}N_7$)), kasugamycin (1L-1,3,4/2,5,6-1-deoxy-2,3,4,5, 6-pentahydroxycyclohexyloxy 2-amino-2,3,4,6-tetradeoxy-4-(α-iminoglycino)-α-D-arabino-hexopyranoside) and mixtures thereof.

In a method of formulating a non-aqueous suspension, solid particles from about 0.1 to about 75% suspension weight and a hydrogenated castor wax or oil from about 0.1 to about 5.0% suspension weight are dispersed into from about 24 to about 99.8% suspension weight of liquid polyalkylene glycol. The solid particles, hydrogenated castor wax or oil, and liquid polyalkylene glycol are mixed until the solid particles are uniformly dispersed in the liquid polyalkylene glycol and the non-aqueous suspension is a pourable or pumpable liquid that achieves a Brookfield viscosity of at least 500 centipoise.

It is therefore an object of the present invention to provide non-aqueous suspensions that are environmentally friendly.

It is another object of the present invention to provide non-aqueous suspensions suitable for use in personal care products, such as cosmetics, shampoos, and the like.

It is still another object of the present invention to provide non-aqueous suspensions that can be manufactured using ingredients suitable for use in indirect contact with food or as a pesticide adjuvant.

It is a further object of the present invention to provide non-aqueous suspensions that are extremely stable over long periods of time and that are operative over a wide temperature range.

It is still a further object of the present invention to provide non-aqueous suspensions that are comprised of materials that are commercially available or easy to manufacture.

Still other objects, features, and advantages of the present invention will become evident to those of ordinary skill in the art in light of the following.

DETAILED DESCRIPTION OF THE PREFERRED EMBODIMENT

A first element of a liquid particle suspension includes solid particles in an amount from 0.1 to 75% of the weight of the suspension. The particles are typically non-polymeric and may be inorganic or organic. Typically the particles of interest will have one or more or the following characteristics that favor use in a concentrated non-aqueous dispersion: 1) low water solubility or materials with high water solubility that have a tendency to have very poor storage, freeze/thaw, and heat/cool stability; 2) the need for a controlled dissolution rate; 3) materials that are reactive with water or a water hydratable agent; 4) materials that cause nuisance dusts; and 5) materials that are easier to meter in liquid form rather than by weighing and pre-dissolving in water when needed at a job site. Typically the particles will have an average particle size between 0.1 micron and 500 microns. More preferably, the particles will have an average particle size between 1 micron and 300 microns. Most preferably the particles will have an average particle size between 5 microns and 200 microns.

Solid particles include a wide variety of materials including inorganic as well as organic solid particles. Illustrative examples of specific solid particles include but are not limited to: peroxides such as magnesium peroxide and calcium peroxide, magnesium oxide, calcium oxide, herbicides including butocarboxime, acephate, dimethoate, dimehypo, vamidothion, methoxyl, dalapon (2,2 dichloropropirionic acid, sodium salt) ammonium sulfamate, dicamba, cacodylic acid, fomesafen; glyphosate, copper sulfate, fosetyl-Al aluminum tris (O-ethyl phosphonate), benalaxyl, guazatine, kasugamycin; insecticides, sulfonated asphalt, salts of sulfonated asphalt, lime, sodium bicarbonate, sodium carbonate, sodium borate, boric acid, potassium nitrate, ammonium dihydrophosphate, ammonium nitrate, sodium nitrate ammonium phosphate, ammonium polyphosphate, potassium hydrogen phosphate, disodium hydrogen phosphate, urea, molybdenum disulfide, pigments, activated carbon, carbon black, unintahite (gilsonite), graphite, iron, iron oxide, zinc, tin, quebracho, lignin, lignite, caustisized lignite, lignosulfonate, chrome lignosulfonate, naphthalenesulfonate; and, combinations of two or more thereof.

A second element of the suspension includes polyalkylene glycol or thickened polyalkylene glycol. The amount of this ingredient varies between about 24 to 99.8% of the weight of the suspension. Particularly preferred are polyethylene glycol, polypropylene glycol or ethylene oxide propylene oxide block copolymers. Most preferred is low molecular weight glycols having a molecular weight of less than 1000, more preferably having a molecular weight between 100 and 600 and most preferably between 200 and 500. Polyethylene glycol having a molecular weight of 200 can also be used, for example. Polyethylene or polypropylene glycol having a molecular weight of 300 or higher and manufactured in accordance with the specifications of the National Formulary can be used in cosmetic grade applications. A technical grade of polyethylene or polypropylene glycol having a molecular weight of 300 or higher as indirect additives for food contact materials and the like may also be used. Technical grades of polyethylene glycol with a molecular weight of 300 or higher are exempt from residue tolerance when used as inert ingredients in pesticide formulations employed in growing crops.

The term "thickened polyalkylene glycol" refers to polyalkylene glycols having a thickener preferably between 0.1 and 4% by weight of the polyalkylene glycol selected from the group consisting of partially neutralized polyacrylic acid, hydroxypropyl cellulose, highly substituted hydroxypropyl guar, hydrated thickening silica including fumed silica and hydrophobic fumed silica, or their functional equivalents or mixtures thereof. The preferred hydrated thickening silicas, also known as thickening silicas, are colloidal gel silicas or hydrophobic derivatives thereof. More preferred ones are Aerosil®200 silica, available from Degussa Corporation, Ridgefield Park N.J., and CAB-O-SIL®M-5 and TS-530 available from Cabot Corporation, Tuscola, Ill. The most preferred is CAB-O-SIL® TS-530.

A third element of the suspension includes a finely divided hydrogenated oil or wax. Most preferably this hydrogenated oil or wax is hydrogenated castor wax. This material is present in the amount from 0.1 to 5% of the weight of the suspension. More preferably in the amount of 0.3 to 3% of the weight of the suspension. Most preferably in the amount of 0.5 to 2% of the weight of the suspension. The preferred hydrogenated castor wax is sold by Süd Chemie of Louisville, Ky. under the name of Rheocin®. Rheocin® is acceptable for use as an indirect food additive in Title 21 of the Code of Federal Regulations.

In addition to the foregoing three elements, the suspension may also contain optional ingredients such as: antifoaming agents, corrosion inhibitors, preservatives, surfactants, water miscible co-solvents, and other materials that aid in the performance of the solid particles in their intended applications.

The suspensions may be used in any number of commercial applications where dry solid particles have previously been used, as well as in applications where solid particles have not been well suited due to their undesirable physical properties, such as low water solubility, stability in concentrated aqueous solutions, the need for a controlled dissolution rate, materials that are reactive with water or a water hydratable suspension agent, materials that cause nuisance dusts, and materials that are easier to meter in liquid form rather than by weighing and pre-dissolving in water when needed at a job site.

The suspensions are particularly useful for applications involving dispersing solid particles in aqueous solutions. Included among such applications are the following: environmental applications (e.g., remediation projects), agricultural applications metal working fluids, paper applications, textile applications, cosmetic or personal care applications, cleaners, detergents, application of pesticides, aerial firefighting applications, construction products (e.g. paint, joint cements, texture finishing compounds and the like), emulsion stabilizers, adhesives, inks, and oil field applications.

EXAMPLES

Example 1
Inventive Suspension Media

A method for making the suspensions of solid particles includes dispersing from 0.1 to 75% suspension weight of a particle and from 0.1 to 5.0% suspension weight of a hydrogenated castor wax or oil into from 24 to 99% suspension weight of polyalkylene glycol. The solid particles, hydrogenated castor wax, and polyalkylene glycol are mixed using conventional agitation, such as an overhead mixer, until the solid particles are uniformly dispersed in the polyalkylene glycol and the hydrogenated castor wax has developed the desired suspension properties. Desirable properties of the suspension include but are not limited to the following:

1. The solvent and suspension stabilizer are environmentally friendly and non-toxic;
2. The particle suspension does not create dust upon addition to water;
3. The suspension remains stable for extremely long periods of time exhibiting minimum separation of solvent and particulate and no packing of the solid particles;
4. The suspension is easily pourable or pumpable;
5. The suspended particles disperse in water better than if the solid is added to water;

Example 2
Sodium Tetraborate Inventive Suspension 810 grams of a powdered anhydrous sodium tetraborate and 20 grams of Rheocine® are dispersed into 1160 grams of pre-thickened polyethylene glycol (200 MW) containing 10 grams thickening silica, specifically CAB-O-SIL® TS-530, in a 2000 ml beaker. The mixture is agitated using an overhead mixer at 700 rpm for a period of 1 hour. At this time the viscosity of the mixture is measured on a Brookfield RV viscometer at 20 rpm using a #4 spindle. A portion of the contents is transferred to a 100 ml graduated cylinder for subsequent measurement of the supernatant separation over time. The balance of the material is transferred to another container for evaluation of particle packing and other properties as desired.

| Composition (% by weight) | |
|---|---|
| Sodium tetraborate | 40.50% |
| Rheocin ® | 1.0% |
| Pre-thickened Polyethylene glycol 200 MW | 58.4% |
| Initial viscosity | 4610 cP |
| Density | 1.365 g/ml |
| Pounds of sodium tetraborate per U.S. Gallon | 4.6 |

| Properties upon aging | Separation | Packing |
|---|---|---|
| 24 hours | 0% | None |
| 3 days | 0% | None |
| 1 month | 1% | None |
| 3 months | 4% | None |

The above composition is easily pourable or pumpable.

Example 3
Sodium Tetraborate Control Suspension

This example compares the suspension properties of anhydrous sodium tetraborate to Example 2 without the use of the hydrogenated castor wax. 810 grams of sodium tetraborate is dispersed into 1170 grams of polyethylene glycol (200 MW) in a 2000 ml beaker. The mixture is agitated using an overhead mixer at 700 rpm for a period of 1 hour. At this time the viscosity of the mixture is measured on a Brookfield RV viscometer at 20 rpm using a #4 spindle. A portion of the contents is transferred to a 100 ml graduated cylinder for subsequent measurement of the supernatant separation over time. The balance of the material is transferred to another container for evaluation of particle packing and other properties as desired.

| Composition (% by weight) | |
|---|---|
| Sodium tetraborate | 40.50% |
| Polyethylene glycol 200 MW | 59.50% |
| Initial viscosity | 1250 cP |
| Density | 1.37 g/ml |
| Pounds per Gallon of Borate Compound | 4.6 |

| Properties on aging | Supernatant separation | Particle packing |
|---|---|---|
| 24 hours | 12% by volume | Medium packed Difficult to remix with stirring rod |
| 3 days | 22% by volume | Hard packed can not remix with stirring rod |
| 1 week | 30% by volume | Hard packed can not remix with stirring rod |

Example 4
Magnesium Peroxide Inventive Suspension 250 grams of a powdered Magnesium Peroxide and 5.0 grams of Rheocin® are dispersed into 240 grams pre-thickened polyethylene glycol (200 MW) containing 5 grams thickening silica, specifically CAB-O-SIL® TS-530a making up the balance in a 600 ml beaker. The mixture is agitated using an overhead mixer at 700 rpm for a period of 1 hour. At this time the viscosity of the mixture is measured on a Brookfield RV viscometer at 20 rpm using a #4 spindle. A portion of the contents is transferred to a 100 ml graduated cylinder for subsequent measurement of the supernatant separation over time. The balance of the material is transferred to another container for evaluation of particle packing and other properties as desired.

| Composition | |
|---|---|
| Magnesium Peroxide | 50% |
| Rheocin ® | 1% |
| Pre-thickened Polyethylene glycol 200 MW | 49% |
| Initial Viscosity | 3200 cP |
| Density | 1.515 g/ml |
| Pounds of magnesium peroxide per U.S. Gallon | 6.3 |

| Properties on aging | Separation | Packing |
|---|---|---|
| 24 hours | 0% | None |
| 3 days | 0% | None |
| 1 month | 1% | None |
| 3 months | 2% | None |

The above compositions are easily pourable or pumpable.

Example 5
Inventive Colemanite Suspension

Turkish Colemanite is an ore rich in calcium borate supplied by American Borate. 240 grams of a powdered Colemanite and 4.5 grams of Rheocin® are dispersed into 207.5 grams pre-thickened polyethylene glycol (200 MW) containing 4.5 grams thickening silica, specifically CAB-O-SIL® TS-530 making up the balance in a 600 ml beaker. The mixture is agitated using an overhead mixer at 700 rpm for a period of 1 hour. At this time the viscosity of the mixture is measured on a Brookfield RV viscometer at 20 rpm using a #4 spindle. A portion of the contents is transferred to a 100 ml graduated cylinder for subsequent measurement of the supernatant separation over time. The balance of the material is transferred to another container for evaluation of particle packing and other properties as desired.

| Composition: | % by weight |
|---|---|
| Colemanite | 53.1% |
| Rheocin ® | 1% |
| Pre-thickened Polyethylene glycol 200 MW | 45.9% |
| Initial Viscosity | 2700 cP |
| Initial density | 1.6 g/ml |
| Pounds of Colemanite per U.S. gallon | 7.1 |

| Properties on aging | Separation | Packing |
|---|---|---|
| 24 hours | 0% | None |
| 7 days | 0% | None |
| 1 month | 1% | None |
| 3 months | 2% | None |

The above compositions are easily pourable or pumpable.

Example 6
Colemanite Control Suspension

This example compares the suspension properties of Colemanite to example 5 without the use of the hydrogenated castor wax suspension agent. 240 grams of a powdered Colemanite and are dispersed into 212 grams pre-thickened polyethylene glycol (200 MW) containing 4.5 grams thickening silica, specifically CAB-O-SIL® TS-530 making up the balance in a 600 ml beaker. The mixture is agitated using an overhead mixer at 700 rpm for a period of 1 hour. At this time the viscosity of the mixture is measured on a Brookfield RV viscometer at 20 rpm using a #4 spindle. A portion of the contents is transferred to a 100 ml graduated cylinder for subsequent measurement of the supernatant separation over time. The balance of the material is transferred to another container for evaluation of particle packing and other properties as desired.

| Composition: | % by weight |
|---|---|
| Colemanite | 53.1% |
| Pre-thickened Polyethylene glycol 200 MW | 46.9% |
| Initial Viscosity | 1100 cP |
| Initial density | 1.6 g/ml |
| Pounds of Colemanite per U.S. gallon | 7.1 |

| Properties on aging | Separation | Packing |
|---|---|---|
| 24 hours | 2% | None |
| 7 days | 22% | Significant settling; difficult to remix |
| 1 month | 27% | Hard packed sediment; very difficult to remix |
| 3 months | 29% | Hard packed sediment; very difficult to remix |

Example 7
Inventive Gilsonite Suspension

Gilsonite is an asphaltic material or solidified hydrocarbon used in a variety of applications in explosives, oil field and other industrial applications. Powdered gilsonite is available from American Gilsonite and others. 100 grams of a powdered gilsonite and 6 grams of Rheocin® are dispersed into 194 grams polyethylene glycol (200 MW) making up the balance in a 600 ml beaker. The mixture is agitated using an overhead mixer at 700 rpm for a period of 1 hour. At this time the viscosity of the mixture is measured on a Brookfield RV viscometer at 20 rpm using a #4 spindle. A portion of the contents is transferred to a 100 ml graduated cylinder for subsequent measurement of the supernatant separation over time. The balance of the material is transferred to another container for evaluation of particle packing and other properties as desired.

| Composition: | % by weight |
|---|---|
| Powdered gilsonite | 33.3% |
| Rheocin ® | 2% |
| Polyethylene glycol 200 MW | 64.7% |
| Initial Viscosity | 3300 cP |
| Initial density | 1.1 g/ml |
| Pounds of gilsonite per U.S. gallon | 3 |

| Properties on aging | Separation | Packing |
|---|---|---|
| 24 hours | 0% | None |
| 7 days | 0% | None |
| 1 month | 0% | None |
| 3 months | 1% | None |

The above compositions are easily pourable or pumpable.

Example 8
Control Gilsonite Suspension

This example compares the suspension properties of gilsonite to example 7 without the use of the hydrogenated castor wax suspension agent. 100 grams of a powdered gilsonite and are dispersed into 200 grams polyethylene glycol (200 MW) making up the balance in a 600 ml beaker. The mixture is agitated using an overhead mixer at 700 rpm for a period of 1 hour. At this time the viscosity of the mixture is measured on a Brookfield RV viscometer at 20 rpm using a #4 spindle. A portion of the contents is transferred to a 100 ml graduated cylinder for subsequent measurement of the supernatant separation over time. The balance of the material is transferred to another container for evaluation of particle packing and other properties as desired.

| Composition: | % by weight | |
| --- | --- | --- |
| Powdered Gilsonite | 33.3% | |
| Polyethylene glycol 200 MW | 66.7% | |
| Initial Viscosity | 360 cP | |
| Initial density | 1.1 g/ml | |
| Pounds of Gilsonite per U.S. gallon | 7.1 | |
| Properties on aging | Separation | Packing (Floating) |
| 24 hours | 19% | Note: Due to the light density of the suspended phase (gilsonite) separation rose to the surface in this case (floated). At 24 hrs it was able to be remixed with some difficulty. |
| 7 days | 22% | Significant floating; difficult to remix |
| 1 month | 33% | The individual particles of gilsonite have coalesced into a continuous phase. This phase solid and can not be remixed without extreme measures. |
| 3 months | 35% | The overall appearance is unchanged from 1 month. The coalesced upper phase has formed a tar like continuous phase which can not be remixed without extreme measures. |

Example 9

Inventive Calcium Aluminate Suspension

Calcium aluminate is an alkaline pH buffer supplied by Sintertec Division of BPI, Inc. It has a low solubility in water, which makes it useful as a controlled release buffer that supplies alkalinity as acid enters a system. The low water solubility of calcium aluminate makes it difficult to supply as an aqueous dispersion of solution. 275 grams of a powdered calcium aluminate and 8 grams of Rheocin® are dispersed into 196 grams pre-thickened polyethylene glycol (200 MW) containing 4 grams thickening silica, specifically CAB-O-SIL® TS-530 making up the balance in a 600 ml beaker. The mixture is agitated using an overhead mixer at 700 rpm for a period of 1 hour. At this time the viscosity of the mixture is measured on a Brookfield RV viscometer at 20 rpm using a #4 spindle. A portion of the contents is transferred to a 100 ml graduated cylinder for subsequent measurement of the supernatant separation over time. The balance of the material is transferred to another container for evaluation of particle packing and other properties as desired.

| Composition: | % by weight | |
| --- | --- | --- |
| Calcium aluminate | 57.4% | |
| Rheocin ® | 1.7% | |
| Pre-thickened Polyethylene glycol 200 MW | 40.1% | |
| Initial Viscosity | 4950 cP | |
| Initial density | 1.9 g/ml | |
| Pounds of calcium aluminate per U.S. gallon | 9.1 | |
| Properties on aging | Separation | Packing |
| 24 hours | 0% | None |
| 7 days | 0% | None |
| 1 month | 1.5% | None |
| 3 months | 3% | None |

The above compositions are easily pourable or pumpable.

Example 10

Control Calcium Aluminate Suspension

This example compares the suspension properties of calcium aluminate to example 9 without the use of the hydrogenated castor wax suspension agent. 275 grams of a powdered calcium aluminate is dispersed into 196 grams pre-thickened polyethylene glycol (200 MW) containing 4 grams thickening silica, specifically CAB-O-SIL® TS-530 making up the balance in a 600 ml beaker. The mixture is agitated using an overhead mixer at 700 rpm for a period of 1 hour. At this time the viscosity of the mixture is measured on a Brookfield RV viscometer at 20 rpm using a #4 spindle. A portion of the contents is transferred to a 100 ml graduated cylinder for subsequent measurement of the supernatant separation over time. The balance of the material is transferred to another container for evaluation of particle packing and other properties as desired.

| Composition: | % by weight | |
| --- | --- | --- |
| Calcium aluminate | 57.4% | |
| Pre-thickened Polyethylene glycol 200 MW | 42.6% | |
| Initial Viscosity | 700 cP | |
| Initial density | 1.85 g/ml | |
| Pounds of Calcium Aluminate per U.S. gallon | 8.9 | |
| Properties on aging | Separation | Packing |
| 24 hours | 2% | None |
| 7 days | 17% | Significant settling; difficult to remix |
| 1 month | 23% | Hard packed sediment; very difficult to remix |

Example 11

Inventive Calcium Carbonate Suspension

Calcium carbonate is widely used in a number of industries as an extender pigment. It is also used in agricultural applications as a pH buffer to adjust the pH of acidic soils. It has a low solubility in water. The low water solubility of calcium carbonate makes it difficult to supply as an aqueous solution. 200 grams of a powdered calcium carbonate and 8 grams of Rheocin® are dispersed into 192 grams pre-thickened polyethylene glycol (200 MW) containing 4 grams thickening silica, specifically CAB-O-SIL® TS-530 making up the balance in a 600 ml beaker. The mixture is agitated using an overhead mixer at 700 rpm for a period of 1 hour. At this time the viscosity of the mixture is measured on a Brookfield RV viscometer at 20 rpm using a #4 spindle. A portion of the contents is transferred to a 100 ml graduated cylinder for subsequent measurement of the supernatant separation over time. The balance of the material is transferred to another container for evaluation of particle packing and other properties as desired.

| Composition: | % by weight |
|---|---|
| Calcium carbonate | 50% |
| Rheocin ® | 2% |
| Pre-thickened Polyethylene glycol 200 MW | 48% |
| Initial Viscosity | 2700 cP |
| Initial density | 1.57 g/ml |
| Pounds of calcium carbonate per U.S. gallon | 6.5 |

| Properties on aging | Separation | Packing |
|---|---|---|
| 24 hours | 0% | None |
| 7 days | 0% | None |
| 1 month | 2% | None |
| 3 months | 3% | None |

The above compositions are easily pourable or pumpable.

Example 12
Control Calcium Carbonate Suspension

This example compares the suspension properties of calcium carbonate to example 11 without the use of the hydrogenated castor wax suspension agent. 200 grams of a powdered calcium carbonate is dispersed into 200 grams pre-thickened polyethylene glycol (200 MW) containing 4 grams thickening silica, specifically CAB-O-SIL® TS-530 making up the balance in a 600 ml beaker. The mixture is agitated using an overhead mixer at 700 rpm for a period of 1 hour. At this time the viscosity of the mixture is measured on a Brookfield RV viscometer at 20 rpm using a #4 spindle. A portion of the contents is transferred to a 100 ml graduated cylinder for subsequent measurement of the supernatant separation over time. The balance of the material is transferred to another container for evaluation of particle packing and other properties as desired.

| Composition: | % by weight |
|---|---|
| Calcium carbonate | 50% |
| Pre-thickened Polyethylene glycol 200 MW | 50% |
| Initial Viscosity | 280 cP |
| Initial density | 1.58 g/ml |
| Pounds of calcium carbonate per U.S. gallon | 6.5 |

| Properties on aging | Separation | Packing |
|---|---|---|
| 24 hours | 12% | None |
| 7 days | 43% | Hard packed sediment; very difficult to remix |
| 1 month | 45% | Hard packed sediment; very difficult to remix |
| 3 months | 45% | Hard packed sediment; very difficult to remix |

Example 13
Inventive Iron Oxide Suspension

Iron (III) oxide ($Fe_2O_3$) is used as a pigment, as a mordant, as a catalyst and on magnetic recording tapes. It is also used as a weighting agent in oil field applications. The low water solubility of $Fe_2O_3$ makes it difficult to supply as an aqueous solution. 390 grams of a Iron (III) oxide which has an average particle size of 5 micrometers and 6 grams of Rheocin® are dispersed into 350 grams pre-thickened polyethylene glycol (200 MW) containing 6 grams thickening silica, specifically CAB-O-SIL® TS-530 making up the balance in a 600 ml beaker. The mixture is agitated using an overhead mixer at 700 rpm for a period of 1 hour. At this time the viscosity of the mixture is measured on a Brookfield RV viscometer at 20 rpm using a #4 spindle. A portion of the contents is transferred to a 100 ml graduated cylinder for subsequent measurement of the supernatant separation over time. The balance of the material is transferred to another container for evaluation of particle packing and other properties as desired.

| Composition: | % by weight |
|---|---|
| $Fe_2O_3$ | 51.9% |
| Rheocin ® | 0.8% |
| Pre-thickened Polyethylene glycol 200 MW | 47.3% |
| Initial Viscosity | 6100 cP |
| Initial density | 1.8 g/ml |
| Pounds of $Fe_2O_3$ per U.S. gallon | 7.8 |

| Properties on aging | Separation | Packing |
|---|---|---|
| 24 hours | 0% | None |
| 7 days | 0% | None |
| 1 month | 0% | None |
| 3 months | 2% | None |

The above compositions are easily pourable or pumpable.

Example 14
Control Iron Oxide Suspension

This example compares the suspension properties of $Fe_2O_3$ to example 13 without the use of the hydrogenated castor wax suspension agent. 390 grams of a $Fe_2O_3$ having an average particle size of 5 micrometers is dispersed into 356 grams pre-thickened polyethylene glycol (200 MW) containing 6 grams thickening silica, specifically CAB-O-SIL® TS-530 making up the balance in a 600 ml beaker. The mixture is agitated using an overhead mixer at 700 rpm for a period of 1 hour. At this time the viscosity of the mixture is measured on a Brookfield RV viscometer at 20 rpm using a #4 spindle. A portion of the contents is transferred to a 100 ml graduated cylinder for subsequent measurement of the supernatant separation over time. The balance of the material is transferred to another container for evaluation of particle packing and other properties as desired.

| Composition: | % by weight |
|---|---|
| $Fe_2O_3$ | 51.9% |
| Pre-thickened Polyethylene glycol 200 MW | 48.1% |
| Initial Viscosity | 3000 cP |
| Initial density | 1.8 g/ml |
| Pounds of $Fe_2O_3$ per U.S. gallon | 7.8 |

| Properties on aging | Separation | Packing |
|---|---|---|
| 24 hours | <1% | None |
| 7 days | <1% | None |
| 1 month | 5% | Slight packing, easy to remix |
| 3 months | 15% | Moderate packing, fairly easy to remix |

Example 15
Inventive Titanium Dioxide Suspension

Titanium dioxide ($TiO_2$) is used as a primary pigment in a variety of coating applications. The low water solubility of $TiO_2$ makes it difficult to supply as an aqueous solution. 250 grams of a $TiO_2$ which has been sifted through a 325 mesh screen and 5 grams of Rheocin® are dispersed into 370 grams pre-thickened polyethylene glycol (200 MW) containing 5 grams thickening silica, specifically CAB-O-SIL® TS-530 making up the balance in a 600 ml beaker. The mixture is agitated using an overhead mixer at 700 rpm for a period of 1 hour. At this time the viscosity of the mixture is measured on a Brookfield RV viscometer at 20 rpm using a #4 spindle. A portion of the contents is transferred to a 100 ml graduated cylinder for subsequent measurement of the supernatant separation over time. The balance of the material is transferred to another container for evaluation of particle packing and other properties as desired.

| Composition: | % by weight | |
|---|---|---|
| $TiO_2$ | 40% | |
| Rheocin ® | 0.8% | |
| Pre-thickened Polyethylene glycol 200 MW | 59.2% | |
| Initial Viscosity | 4200 cP | |
| Initial density | 1.57 g/ml | |
| Pounds of $TiO_2$ per U.S. gallon | 5.2 | |
| Properties on aging | Separation | Packing |
| 24 hours | 0% | None |
| 7 days | 0% | None |
| 1 month | 0% | None |
| 3 months | <1% | None |

The above compositions are easily pourable or pumpable.

Example 16
Control Titanium Dioxide Suspension

This example compares the suspension properties of $TiO_2$ to example 15 without the use of the hydrogenated castor wax suspension agent. 250 grams of a $TiO_2$ which had been sifted through a 325 mesh screen is dispersed into 370 grams pre-thickened polyethylene glycol (200 MW) containing 5 grams thickening silica, specifically CAB-O-SIL® TS-530 making up the balance in a 600 ml beaker. The mixture is agitated using an overhead mixer at 700 rpm for a period of 1 hour. At this time the viscosity of the mixture is measured on a Brookfield RV viscometer at 20 rpm using a #4 spindle. A portion of the contents is transferred to a 100 ml graduated cylinder for subsequent measurement of the supernatant separation over time. The balance of the material is transferred to another container for evaluation of particle packing and other properties as desired.

| Composition: | % by weight | |
|---|---|---|
| $TiO_2$ | 40% | |
| Pre-thickened Polyethylene glycol 200 MW | 60% | |
| Initial Viscosity | 2100 cP | |
| Initial density | 1.57 g/ml | |
| Pounds of $TiO_2$ per U.S. gallon | 5.2 | |
| Properties on aging | Separation | Packing |
| 24 hours | <1% | None |
| 7 days | <1% | None |
| 1 month | 7% | Slight packing, fairly easy to remix |
| 3 months | 13% | Moderate packing; fairly easy to remix |

Example 17
Inventive Calcium Lignosulfonate Suspension

Calcium lignosulfonate is widely used in a number of industries, including oil well cements, as a dispersant. It has a low solubility in water. The low water solubility of calcium lignosulfonate makes it difficult to supply as an aqueous solution. 105 grams of a powdered calcium lignosulfonate and 3 grams of Rheocin® are dispersed into 192 grams pre-thickened polyethylene glycol (200 MW) containing 3 grams thickening silica, specifically CAB-O-SIL® TS-530 making up the balance in a 600 ml beaker. The mixture is agitated using an overhead mixer at 700 rpm for a period of 1 hour. At this time the viscosity of the mixture is measured on a Brookfield RV viscometer at 20 rpm using a #4 spindle. A portion of the contents is transferred to a 100 ml graduated cylinder for subsequent measurement of the supernatant separation over time. The balance of the material is transferred to another container for evaluation of particle packing and other properties as desired.

| Composition: | % by weight | |
|---|---|---|
| Calcium lignosulfonate | 35% | |
| Rheocin ® | 1% | |
| Pre-thickened Polyethylene glycol 200 MW | 64% | |
| Initial Viscosity | 1800 cP | |
| Initial density | 1.13 g/ml | |
| Pounds of calcium lignosulfonate per U.S. gallon | 3.3 | |
| Properties on aging | Separation | Packing |
| 24 hours | 0% | None |
| 7 days | 0% | None |
| 1 month | 0% | None |
| 3 months | 0% | None |

The above compositions are easily pourable or pumpable.

Example 18
Control Calcium Lignosulfonate Suspension

This example compares the suspension properties of calcium lignosulfonate to example 17 without the use of the hydrogenated castor wax suspension agent. 105 grams of a powdered calcium lignosulfonate is dispersed into 195 grams polyethylene glycol (200 MW) making up the balance in a 600 ml beaker. The mixture is agitated using an overhead mixer at 700 rpm for a period of 1 hour. At this time the viscosity of the mixture is measured on a Brookfield RV viscometer at 20 rpm using a #4 spindle. A portion of the contents is transferred to a 100 ml graduated cylinder for subsequent measurement of the supernatant separation over time. The balance of the material is transferred to another container for evaluation of particle packing and other properties as desired.

| Composition: | % by weight |
|---|---|
| Calcium lignosulfonate | 35% |
| Polyethylene glycol 200 MW | 65% |
| Initial Viscosity | 860 cP |
| Initial density | 1.13 g/ml |
| Pounds of calcium lignosulfonate per U.S. gallon | 3.3 |

Properties on aging  Separation Packing

| | | |
|---|---|---|
| 24 hours | 5% | Separation in the middle of the column easy to remix |
| 7 days | 24% | Triphase separation. Upper phase crusty and sticky, middle phase is clear liquid, bottom phase is hard packed; difficult to remix |
| 1 month | 24% | Triphase separation. Upper phase crusty and sticky, middle phase is clear liquid, bottom phase is hard packed; difficult to remix |
| 3 months | 26% | Triphase separation. Upper phase crusty and sticky, middle phase is clear liquid, bottom phase is hard packed; difficult to remix |

Example 19
Inventive Ethylenediaminetetraacetic Acid Suspension

Ethylenediaminetetraacetic acid (EDTA) is a well known chelating agent for metal ions. EDTA is used in a wide variety of applications including agriculture, cleaning products, oilfield, paper, personal care, and metal working among others. The low water solubility of EDTA (<0.1% at 25° C.) makes it difficult to supply as an aqueous solution in the acid form. EDTA is frequently converted to a salt to achieve water solubility, but this is an unnecessary if the system pH is acidic and the concentration at use dilution is soluble. 122.5 grams of a EDTA and 7 grams of Rheocin® are dispersed into 221.5 grams pre-thickened polyethylene glycol (200 MW) containing 3.5 grams thickening silica, specifically CAB-O-SIL® TS-530 making up the balance in a 600 ml beaker. The mixture is agitated using an overhead mixer at 700 rpm for a period of 1 hour. At this time the viscosity of the mixture is measured on a Brookfield RV viscometer at 20 rpm using a #4 spindle. A portion of the contents is transferred to a 100 ml graduated cylinder for subsequent measurement of the supernatant separation over time. The balance of the material is transferred to another container for evaluation of particle packing and other properties as desired.

| Composition: | % by weight | |
|---|---|---|
| EDTA | 35% | |
| Rheocin ® | 1% | |
| Pre-thickened Polyethylene glycol 200 MW | 63% | |
| Initial Viscosity | 3100 cP | |
| Initial density | 1.29 g/ml | |
| Pounds of EDTA per U.S. gallon | 3.76 | |
| Properties on aging | Separation | Packing |
| 24 hours | 0% | None |
| 7 days | 0% | None |
| 1 month | <1% | None |
| 3 months | 2% | None |

The above compositions are easily pourable or pumpable.

Example 20
Control Ethylenediaminetetraacetic Acid Suspension

This example compares the suspension properties of EDTA to example 19 without the use of the hydrogenated castor wax suspension agent. 129 grams of a EDTA is dispersed into 240 grams polyethylene glycol (200 MW) making up the balance in a 600 ml beaker. The mixture is agitated using an overhead mixer at 700 rpm for a period of 1 hour. At this time the viscosity of the mixture is measured on a Brookfield RV viscometer at 20 rpm using a #4 spindle. A portion of the contents is transferred to a 100 ml graduated cylinder for subsequent measurement of the supernatant separation over time. The balance of the material is transferred to another container for evaluation of particle packing and other properties as desired.

| Composition: | % by weight | |
|---|---|---|
| EDTA | 35% | |
| Polyethylene glycol 200 MW | 65% | |
| Initial Viscosity | 300 cP | |
| Initial density | 1.26 g/ml | |
| Pounds of EDTA per U.S. gallon | 3.7 | |
| Properties on aging | Separation | Packing |
| 24 hours | 43% | Soft packing, difficult to remix |
| 7 days | 46% | Hard packing, very difficult to remix |
| 1 month | 48% | Hard packing, very difficult to remix |
| 3 months | 51% | Hard packing, very difficult to remix |

Although the present invention has been described in terms of the foregoing embodiment, such description has been for exemplary purposes only and, as will be apparent to one of ordinary skill in the art, many alternatives, equivalents, and variations of varying degrees will fall within the scope of the present invention. That scope, accordingly, is not to be limited in any respect by the foregoing description; rather, it is defined only by the claims that follow.

I claim:

1. A non-aqueous suspension, comprising:
   (a) solid particles;
   (b) liquid polyalkylene glycol into which the solid particles are dispersed; and
   (c) a suspension stabilizer comprising a hydrogenated castor oil or wax, whereby the non-aqueous suspension of the solid particles is a pourable or pumpable liquid.

2. The non-aqueous suspension according to claim 1 wherein the polyalkylene glycol is selected from the group consisting of polyethylene glycol, polypropylene glycol ethylene oxide propylene oxide block copolymers, and mixtures thereof.

3. The non-aqueous suspension according to claim 1 wherein the amount of suspension stabilizer comprises between about 0.1 and about 5.0 percent by weight of the suspension.

4. The non-aqueous suspension according to claim 1 wherein the solid particles comprise inorganic particles.

5. The non-aqueous suspension according to claim 4 wherein the solid particles comprise boron compounds.

6. The non-aqueous suspension according to claim 4 wherein the solid particles comprise alkaline earth peroxides.

7. The non-aqueous suspension according to claim 4 wherein the solid particles comprise magnesium peroxide or calcium peroxide.

8. The non-aqueous suspension according to claim 4 wherein the solid particles comprise iron oxide.

9. The non-aqueous suspension according to claim 4 wherein the solid particles comprise calcium aluminate.

10. The non-aqueous suspension according to claim 4 wherein the solid particles comprise calcium carbonate, magnesium carbonate, calcium oxide, magnesium oxide, calcium hydroxide and magnesium hydroxide and mixtures thereof.

11. The non-aqueous suspension according to claim 4 wherein the particles comprise siliceous or ceramic particles.

12. The non-aqueous suspension according to claim 1 wherein the solid particles comprise organic particles.

13. The non-aqueous suspension according to claim 12 wherein the particles comprise gilsonite.

14. The non-aqueous suspension according to claim 12 wherein the solid particles comprise lignosulfonates and the sodium, potassium, ammonium, calcium and magnesium salts thereof.

15. The non-aqueous suspension according to claim 12 wherein the solid particles comprise ethylenediaminetetraacetic acid and the salts thereof.

16. The non-aqueous suspension according to claim 1, further comprising one or more of the following additive materials selected from the group consisting of proppants, antifoaming agents, surfactants, corrosion inhibitors, pH buffers, and preservatives.

17. The non-aqueous suspension according to claim 1 wherein the particles comprise an average particle size of about 0.1 to about 600 microns.

18. The non-aqueous suspension according to claim 1 wherein the particles comprise an average particle size of 1 to 300 microns.

19. The non-aqueous suspension according to claim 1 wherein the particles comprise an average particle size of 5 to 200 microns.

20. The non-aqueous suspension according to claim 1 wherein the liquid polyalkylene glycol further comprises between about 0.1 and 4% by weight of the liquid polyalkylene glycol of a thickener selected from the group consisting of partially neutralized polyacrylic acid, hydroxypropyl cellulose, hydroxypropyl guar, fumed silica, hydrophobic silica, and mixtures thereof.

21. The non-aqueous suspension according to claim 1 wherein the particles comprise fertilizers selected from the group consisting of potassium nitrate, ammonium dihydrogenphosphate, ammonium nitrate, sodium nitrate ammonium phosphate, ammonium polyphosphate, potassium hydrogen phosphate, disodium hydrogen phosphate, urea, and mixtures thereof.

22. The non-aqueous suspension according to claim 1 wherein the particles comprise pesticides selected from the group consisting of boric acid, butocarboxime, O,S,-dimethyl acetylphosphoramidothioate, dimethoate, disodium salt of dihydrogen S,S'-(2-dimethylaminotrimethylene)di(thiosulfate), O,O-dimethyl S-2-(1-methylcarbamoylethylthio)ethyl phosphorothioate, S-methyl (EZ)-N-(methylcarbamoyloxy)thioacetamide and mixtures thereof.

23. The non-aqueous suspension according to claim 1 wherein the particles comprise herbicides selected from the group consisting of 2,2-dichloropropirionic acid (2,2 dichloropropirionic acid, sodium salt), ammonium sulfamate, 3,6-dicloro-o-anisic acid, cacodylic acid, 5-(2-chloro-α,α,α-trifluoro-p-tolyloxy)-N-methylsulfonyl-2-nitrobenzamide; N-(phosphonomethyl)glycine and mixtures thereof.

24. The non-aqueous suspension according to claim 1 wherein the particles comprise fungicides selected from the group consisting of copper sulfate, ethyl hydrogen phosphonate aluminum tris (O-ethyl phosphonate), methyl N-phenylacetyl-N-2,6-xylyl-DL-alaninate, iminoctadine ($C_{38}H_{41}N_7$), 1L-1,3,4/2,5,6-1-deoxy-2,3,4,5,6-pentahydroxycyclohexyloxy 2-amino-2,3,4,6-tetradeoxy-4-(α-iminoglycino)-αD-arabino-hexopyranoside and mixtures thereof.

25. The non-aqueous suspension according to claim 1 wherein the solid particles comprise non-polymeric particles.

26. The non-aqueous suspension according to claim 1 wherein the amount of the solid particles comprises between about 0.1 and about 75 percent by weight of the suspension.

27. The non-aqueous suspension according to claim 1 wherein the amount of polyalkylene glycol comprises between about 24 and about 99 percent by weight of the suspension.

28. A composition comprising environmental chemical; agricultural chemical; paper chemical; textile chemical; construction or building product ingredient comprising paint, joint cement, textured finishing compound; cosmetic ingredients; hair spray; gelatin substitute; ceramic material; cleaning composition; polish; ink; fire-fighting chemical; metal-working chemical; adhesive chemical; explosive chemical; flocculent; water treatment compound; binder chemical for sand; ores or coal or oil field chemical that includes a non-aqueous suspension, comprising:

(a) solid particles;
(b) liquid polyalkylene glycol into which the solid particles are dispersed; and
(c) a suspension stabilizer comprising a hydrogenated castor oil or wax, whereby the non-aqueous suspension of the solid particles is a pourable or pumpable liquid.

29. The non-aqueous suspension according to claim 28 wherein the polyalkylene glycol is selected from the group consisting of polyethylene glycol, polypropylene glycol, ethylene oxide propylene oxide block copolymers, and mixtures thereof.

30. The non-aqueous suspension according to claim 28 wherein the amount of suspension stabilizer comprises between about 0.1 and about 5.0 percent by weight of the suspension.

31. The non-aqueous suspension according to claim 28 wherein the solid particles comprise inorganic particles.

32. The non-aqueous suspension according to claim 31 wherein the solid particles comprise boron compounds.

33. The non-aqueous suspension according to claim 31 wherein the solid particles comprise alkaline earth peroxides.

34. The non-aqueous suspension according to claim 31 wherein the solid particles comprise magnesium peroxide or calcium peroxide.

35. The non-aqueous suspension according to claim 31 wherein the solid particles comprise iron oxide.

36. The non-aqueous suspension according to claim 31 wherein the solid particles comprise calcium aluminate.

37. The non-aqueous suspension according to claim 31 wherein the solid particles comprise calcium carbonate, magnesium carbonate, calcium oxide, magnesium oxide, calcium hydroxide and magnesium hydroxide and mixtures thereof.

38. The non-aqueous suspension according to claim 31 wherein the particles comprise siliceous or ceramic particles.

39. The non-aqueous suspension according to claim 28 wherein the solid particles comprise organic particles.

40. The non-aqueous suspension according to claim 39 wherein the particles comprise gilsonite.

41. The non-aqueous suspension according to claim 39 wherein the solid particles comprise lignosulfonates and the sodium, potassium, ammonium, calcium and magnesium salts thereof.

42. The non-aqueous suspension according to claim 39 wherein the solid particles comprise ethylenediaminetetraacetic acid and the salts thereof.

43. The non-aqueous suspension according to claim 28, further comprising one or more of the following additive materials selected from the group consisting of proppants, antifoaming agents, surfactants, corrosion inhibitors, pH buffers, and preservatives.

44. The non-aqueous suspension according to claim 28 wherein the particles comprise an average particle size of about 0.1 to about 600 microns.

45. The non-aqueous suspension according to claim 28 wherein the particles comprise an average particle size of 1 to 300 microns.

46. The non-aqueous suspension according to claim 28 wherein the particles comprise an average particle size of 5 to 200 microns.

47. The non-aqueous suspension according to claim 28 wherein the liquid polyalkylene glycol further comprises between about 0.1 and 4% by weight of the liquid polyalkylene glycol of a thickener selected from the group consisting of partially neutralized polyacrylic acid, hydroxypropyl cellulose, hydroxypropyl guar, fumed silica, hydrophobic silica, and mixtures thereof.

48. The non-aqueous suspension according to claim 28 wherein the particles comprise fertilizers selected from the group consisting of potassium nitrate, ammonium dihydrogenphosphate, ammonium nitrate, sodium nitrate ammonium phosphate, ammonium polyphosphate, potassium hydrogen phosphate, disodium hydrogen phosphate, urea, and mixtures thereof.

49. The non-aqueous suspension according to claim 28 wherein the particles comprise pesticides selected from the group consisting of boric acid, butocarboxime, O,S,-dimethyl acetylphosphoramidothioate dimethoate, disodium salt of dihydrogen S,S'-(2-dimethylaminotrimethylene)di (thiosulfate) O,O-dimethyl S-2-(1-methylcarbamoylethylthio)ethyl phosphorothioate, S-methyl (EZ)-N-(methylcarbamoyloxy)thioacetamide and mixtures thereof.

50. The non-aqueous suspension according to claim 28 wherein the particles comprise herbicides selected from the group consisting of 2,2-dichloropropirionic acid (2,2 dichloropropirionic acid, sodium salt), ammonium sulfamate, 3,6-dicloro-o-anisic acid, cacodylic acid, 5-(2-chloro-α,α,α-trifluoro-p-tolyloxy)-N-methylsulfonyl-2-nitrobenzamide N-(phosphonomethyl)glycine and mixtures thereof.

51. The non-aqueous suspension according to claim 28 wherein the particles comprise fungicides selected from the group consisting of copper sulfate, ethyl hydrogen phosphonate aluminum tris (O-ethyl phosphonate), methyl N-phenylacetyl-N-2,6-xylyl-DL-alaninate, iminoctadine ($C_{18}H_{41}N7$), 1L-1,3,4/2,5,6-1-deoxy-2,3,4,5,6- pentahydroxycyclohexyloxy 2-amino-2,3,4,6-tetradeoxy-4-(α-iminoglycino)-α-D-arabino-hexopyranoside and mixtures thereof.

52. The non-aqueous suspension according to claim 28 wherein the solid particles comprise non-polymeric particles.

53. The non-aqueous suspension according to claim 28 wherein the amount of the solid particles comprises between about 0.1 and about 75 percent by weight of the suspension.

54. The non-aqueous suspension according to claim 28 wherein the amount of polyalkylene glycol comprises between about 24 and about 99 percent by weight of the suspension.

55. A method of formulating a non-aqueous suspension, comprising:

dispersing solid particles and a hydrogenated castor wax or oil into liquid polyalkylene glycol, and mixing the solid particles, the hydrogenated castor wax or oil, and the liquid polyalkylene glycol until the solid particles are uniformly dispersed in the liquid polyalkylene glycol and the non-aqueous suspension of the solid particles is a pourable or pumpable liquid that achieves a Brookfield viscosity of at least 500 centipoise.

56. The method according to claim 55 wherein the solid particles are dispersed in an amount from between about 0.1 and about 75 percent by weight of the suspension.

57. The method according to claim 55 wherein the hydrogenated castor wax or oil is dispersed in an amount between about 0.1 and about 5.0 percent by weight of the suspension.

58. The method according to claim 55 wherein the amount of polyalkylene glycol comprises between about 24 and about 99 percent by weight of the suspension.

59. The method according to claim 55 wherein the polyalkylene glycol is selected from the group consisting of polyethylene glycol, polypropylene glycol, ethylene oxide propylene oxide block copolymers, and mixtures thereof.

60. The method according to claim 55 wherein the solid particles comprise inorganic particles.

61. The method according to claim 60 wherein the solid particles comprise boron compounds.

62. The method according to claim 60 wherein the solid particles comprise alkaline earth peroxides.

63. The method according to claim 60 wherein the solid particles comprise magnesium peroxide or calcium peroxide.

64. The method according to claim 60 wherein the solid particles comprise iron oxide.

65. The method according to claim 60 wherein the solid particles comprise calcium aluminate.

66. The method according to claim 60 wherein the solid particles comprise calcium carbonate, magnesium carbonate, calcium oxide, magnesium oxide, calcium hydroxide and magnesium hydroxide and mixtures thereof.

67. The method according to claim 60 wherein the particles comprise siliceous or ceramic particles.

68. The method according to claim 55 wherein the solid particles comprise organic particles.

69. The method according to claim 68 wherein the particles comprise gilsonite.

70. The method according to claim 68 wherein the solid particles comprise lignosulfonates and the sodium, potassium, ammonium, calcium and magnesium salts thereof.

71. The method according to claim 68 wherein the solid particles comprise ethylenediaminetetraacetic acid and the salts thereof.

72. The method according to claim 55, further comprising one or more of the following additive materials selected from the group consisting of proppants, antifoaming agents, surfactants, corrosion inhibitors, pH buffers, and preservatives.

73. The method according to claim 55 wherein the particles comprise an average particle size of about 0.1 to about 600 microns.

74. The method according to claim 55 wherein the particles comprise an average particle size of 1 to 300 microns.

75. The method according to claim 55 wherein the particles comprise an average particle size of 5 to 200 microns.

76. The method according to claim 55 wherein the liquid polyalkylene glycol further comprises between about 0.1 and 4% by weight of the liquid polyalkylene glycol of a thickener selected from the group consisting of partially neutralized polyacrylic acid) hydroxypropyl cellulose, hydroxypropyl guar, fumed silica, hydrophobic silica, and mixtures thereof.

77. The method according to claim 55 wherein the particles comprise fertilizers selected from the group consisting of potassium nitrate, ammonium dihydrogenphosphate, ammonium nitrate, sodium nitrate ammonium phosphate, ammonium polyphosphate, potassium hydrogen phosphate, disodium hydrogen phosphate, urea, and mixtures thereof.

78. The method according to claim 55 wherein the particles comprise pesticides selected from the group consisting of boric acid, butocarboxime, O,S,-dimethyl acetylphosphoramidothioate, dimethoate, disodium salt of dihydrogen S,S'-(2-dimethylaminotrimethylene)di(thiosulfate) O,O-dimethyl S-2-(1-methylcarbamoylethylthio)ethyl phosphorothioate, S-methyl (EZ)-N-(methylcarbamoyloxy)thioacetamide and mixtures thereof.

79. The method according to claim 55 wherein the particles comprise herbicides selected from the group consisting of 2,2-dichloropropirionic acid (2,2 dichloropropirionic acid, sodium salt), ammonium sulfamate, 3,6-dicloro-o-anisic acid, cacodylic acid, 5-(2-chloro-α,α,α-trifluoro-p-tolyloxy)-N-methylsulfonyl-2-nitrobenzamide; N-(phosphonomethyl)glycine and mixtures thereof.

80. The method according to claim 55 wherein the particles comprise fungicides selected from the group consisting of copper sulfate, ethyl hydrogen phosphonate aluminum tris (O-ethyl phosphonate), methyl N-phenylacetyl-N-2,6-xylyl-DL-alaninate, iminoctadine ($C_{18}H_{41}N_7$), 1L-1,3,4/2,5,6-1-deoxy-2,3,4,5,6-pentahydroxycyclohexyloxy 2-amino-2,3,4,6-tetradeoxy-4-(α-iminoglycino)-α-D-arabino-hexopyranoside and mixtures thereof. -2,3,4,6-tetradeoxy-4-(α-iminoglycino)-α-D-arabino-hexopyranoside and mixtures thereof.

81. The method according to claim 55 wherein the solid particles comprise non-polymeric particles.

* * * * *